United States Patent [19]
Sabater et al.

[11] Patent Number: 4,931,659
[45] Date of Patent: Jun. 5, 1990

[54] DEVICE FOR CALIBRATING AN APPARATUS FOR MEASURING THE FORMATION INDEX OF A SHEET OF PAPER

[75] Inventors: Jacques Sabater, Gif sur Yvette; Gérard Gillet, Biviers, both of France

[73] Assignee: Centre Tech. de L'Industie des Papiers cartons etc., France

[21] Appl. No.: 196,728

[22] Filed: May 20, 1988

[30] Foreign Application Priority Data

May 27, 1987 [FR] France .................. 87 07660

[51] Int. Cl.⁵ .............................................. G01N 21/86
[52] U.S. Cl. .................... 250/571; 356/429; 356/432
[58] Field of Search ............... 250/227, 562, 563, 571, 250/572; 356/432, 239, 429

[56] References Cited

U.S. PATENT DOCUMENTS

| | | | |
|---|---|---|---|
| 3,803,414 | 4/1974 | Van Horne et al. | 250/339 |
| 4,224,513 | 9/1980 | Casey et al. | 250/571 |
| 4,231,663 | 11/1980 | Phillippi | 356/432 |
| 4,319,847 | 3/1982 | Howarth | 250/571 |

FOREIGN PATENT DOCUMENTS 0169790 12/1986 European Pat. Off. .

Primary Examiner—Edward P. Westin
Attorney, Agent, or Firm—Wall and Roehrig

[57] ABSTRACT

A device for calibrating an apparatus for measuring the formation index of a sheet of paper in which an emitted light beam is directed through the sheet of paper and detected and electronically processed into a modulated output signal. The device has a frosted glass for diffusing the measuring beam of light and an opaque rod mounted for rotation in and out of the beam of light so as to provide a modulation of the detected light of a known amount which can then be used to calibrate the measuring apparatus by adjusting the various parameters of the apparatus to yield the desired known output modulation.

7 Claims, 2 Drawing Sheets

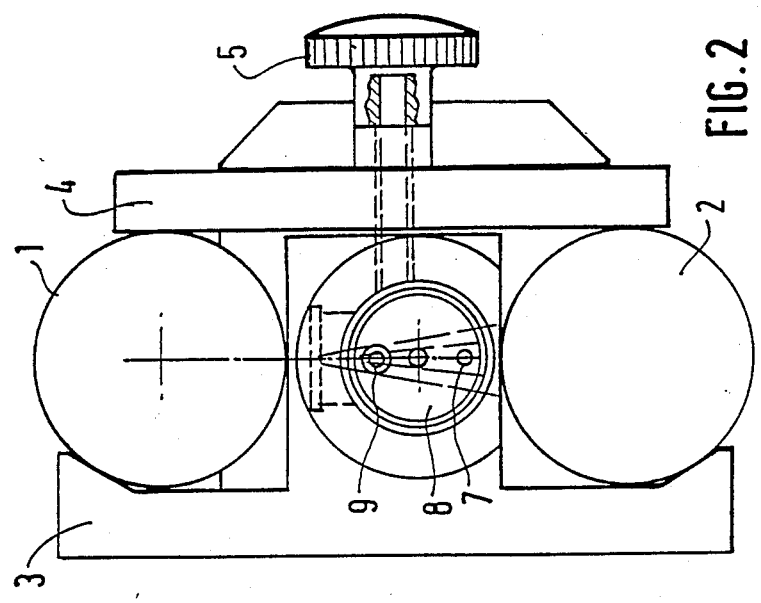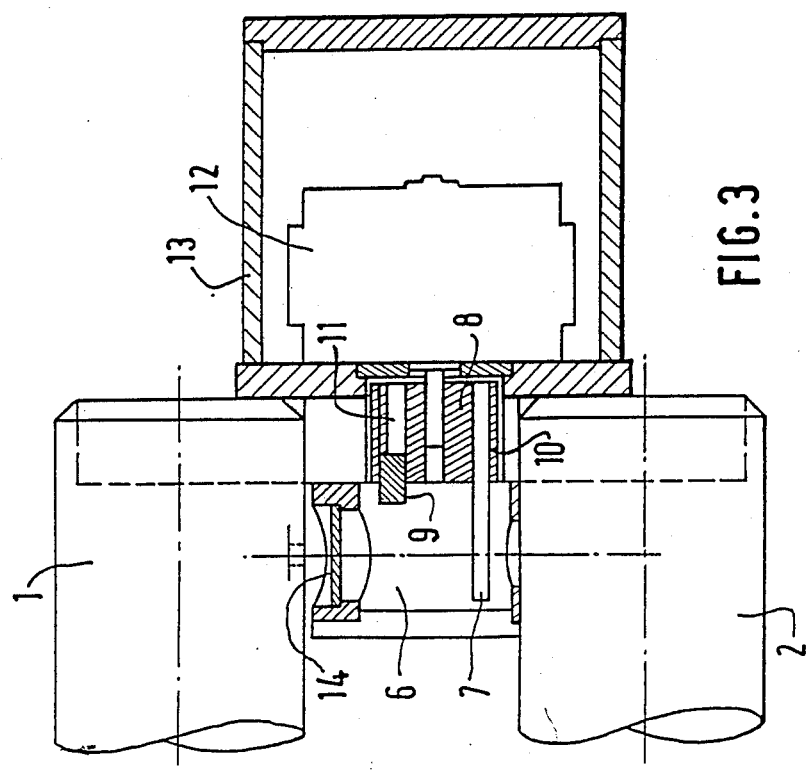

DEVICE FOR CALIBRATING AN APPARATUS FOR MEASURING THE FORMATION INDEX OF A SHEET OF PAPER

CROSS REFERENCE

This application is related to U.S. Pat. No. 4,707,223 issued Nov. 17, 1987 to Sabater et al. and assigned to the common assignee of this application.

BACKGROUND OF THE INVENTION

The present invention relates to a device for calibrating an apparatus for measuring the formation index of a sheet of paper. It relates, in particular, to a device for calibrating an apparatus for continuously measuring the characteristics of a sheet of paper, said apparatus being commonly referred to by a person skilled in the art as a "formation sensor".

In the paper-making industry, the concept of formation involves the regular distribution and amount of the fibrous material in the plane of a sheet of paper which, together with the basis weight components, determine the characteristics of the paper. In the above patent, Applicant described a formation sensor comprising fundamentally a light source directing a polarized laser beam through the sheet of paper to be analyzed, a polarizer, the axis of polarization of which is perpendicular to the axis of polarization of the emitted laser beam, a means for sensing the transmitted laser beam, and for converting the latter into an electrical signal, and electronic processing means for separating this electrical signal into two components and for computing, from these components, the index I representing the formation index. The formation index I is defined as follows:

$$I = \frac{\text{effective } RMS \text{ value at the instant } t}{\text{mean value } M \text{ at the same instant } t}$$

where RMS commonly designates the effective variable value of the laser beam transmitted through the sheet, commonly referred to as the formation component, and the value M is the mean value of the transmitted signal, commonly referred to as the basis weight component.

The formation sensor generally comprises a U-shaped chassis between the branches of which the sheet of paper to be analyzed passes continuously and at constant speed. The upper branch of the U contains the laser, of the He-Ne type, and the lower branch the polarizer and the system for receiving the transmitted laser beam.

In order to calibrate such a device, it is necessary to have a standard available which produces a modulation of the optical signal which is detectable by the system for receiving the transmitted laser beam.

The calibration process is essential for at least two reasons:

1. the paper-making industry is moving toward requiring objective measurement of differences in paper characteristics which, until the appearance on the market of devices of the present type, were very subjective, being determined by visual examination of the transparency of the sheet of paper.

2. the possible appearance of drifts in the results of the measurements made by the formation sensor, due to inherent aging of the electronic system and the optical components of the device.

OBJECTS AND SUMMARY OF THE INVENTION

It is an object of the present invention to provide a device for calibrating a formation sensor by measuring one or more known formation indices.

It is another object to provide a calibration device having known indices which are measured by said formation sensor, in order to verify the validity of the paper measurements made by the sensor.

The objects of the present invention are accomplished in one embodiment by a device for calibrating an apparatus for measuring the formation index of a sheet of paper, of the type in which a beam of light is directed through said sheet, and then the transmitted radiation is received and analyzed. The calibrating device replaces the paper to be measured which has a formation index which is not strictly constant by a device simulating the same optical properties as said material, but exhibiting a formation index which is a known constant.

Advantageously, in practice the calibrating device includes a diffusing means which is a frosted or diffusing material, such as, for example, frosted glass, frosted translucent plastic material, sheets of paper and the like; and modulating means consisting of an obstacle that absorbs or blocks the light at least partially by periodically cutting the light beam.

The absorbing obstacle is an index, or rod, mounted on a rotatable disk which is disposed in a plane parallel to the emitted light beam, said rotatable disk further including a balancing weight mounted on the other end of a diameter through said rod to balance said drive for smooth rotation.

The calibrating device includes clamping jaws, intended to permit its mounting at the end of the two branches of the U-shaped chassis, in the optical path of the laser beam and a light shield to prevent interference from unwanted reflections.

The manner in which the invention may be implemented and the advantages which arise therefrom will become more clearly evident from the embodiment which follows, which is given on an indicative and non-limiting basis in support of the accompanying figures.

BRIEF DESCRIPTION OF THE DRAWINGS

FIG. 2 is a transverse cross-section of the device according to the invention, in position on a formation sensor to be calibrated;

FIG. 3 is a partial longitudinal cross-section of the device according to the invention, still in position on the formation sensor to be calibrated.

DETAILED DESCRIPTION OF THE PREFERRED EMBODIMENT

Figure 1:
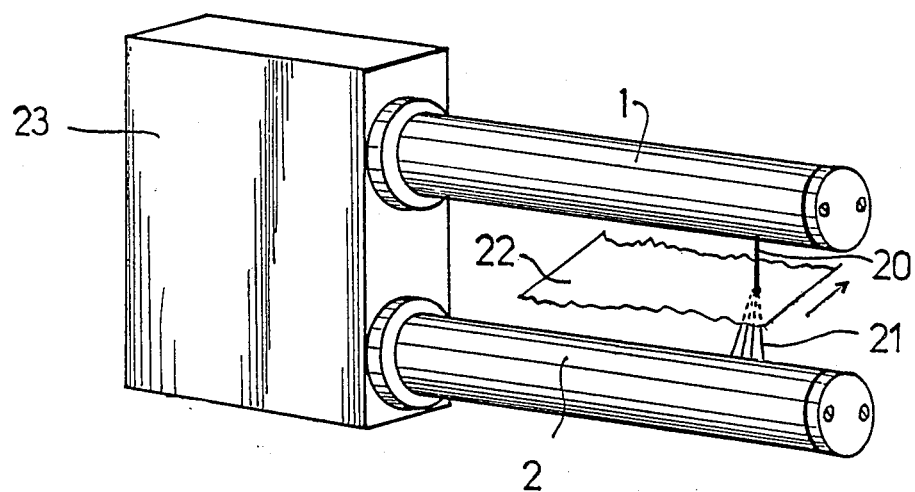
FIG. 1 is a partial diagrammatic view of a formation sensor intended to be calibrated by means of the device according to the invention.

As can be seen in FIG. 1, the formation sensor to be calibrated comprises a U-shaped chassis 23, one of the branches 1 of which encloses a helium-neon laser source emitting a beam 20, and the other branch 2 of which comprises means for receiving the laser beam emanating from said source, means for converting the laser signal into an electrical signal, and electronic means for processing said electrical signal (not shown). These two branches 1 and 2 of the U-shaped chassis 23 are constructed of anodized aluminum.

A sheet of paper 22 is fed continuously between the two branches 1 and 2 of the formation sensor causing a diffusion and a modulation of the emitted laser beam 20, converting the latter into a beam 21, received at the location of the branch 2.

The device according to the invention has clamping jaws 3 and 4 (FIG. 2), intended to firmly mount it on a temporary basis to the formation sensor described hereinabove. The mounting is accomplished in a known manner by screwing the knurled knob 5, which forms a solid unit with the jaw 3, the jaw 4 being pierced by a threaded hole, fulfilling the function of nut for the knob 5. Said jaws are supported on the branches 1 and 2 of the formation sensor thus assuring a self-centering of the assembly.

The calibrating device according to the invention has a protective cage 6, in the form of a truncated cylinder. The latter is constructed of aluminum and its internal surface is a blackened, matte finish in order to eliminate unwanted reflections, since spurious reflections could cause errors in the calibration.

As can be seen in FIGS. 2 and 3, the calibrating device according to the invention comprises a removable absorbing index or rod 7, mounted in a slot 10 formed in a rotatable disk 8, the axis of rotation of which is perpendicular to the axis of the emitted laser beam 20. This rotatable disk 8 is activated by means of a conventional electric motor 12, driven by direct current, protected externally by means of a cover 13. In order to dynamically balance the rotatable disk 8, a weight 9, which is likewise removable, and of the same mass as the absorbing index 7, is mounted in a slot 11, situated in said disk 8. Weight 9 is symmetrically located in relation to its axis of rotation and index 7.

It should be noted that the absorbing index 7 is in the form of a cylindrical bar and is matte black, in order to avoid spurious reflections. Its diameter is chosen to correspond to a particular set of characteristics. Other diameters may be chosen in order to be able to simulate a variety of formation indices The "standard" formation index is established as a function of the modulation induced by a known modulating and diffusing rod. Variation of the diameter of the cylindrical absorbing index 7 causes a variation in the modulation level, and therefore in the formation index. The amplitude of the modulation becomes greater as the diameter increases.

It is self-evident that the index 7 may likewise be permanently mounted on the rotatable disk 8 for some embodiments, and that any replacement of the index 7 likewise implies the replacement of the weight 9. In fact, the latter must always be of the same mass as the index 7, on account of the design of the device.

It should be noted that the device according to the invention is designed in such a manner that when this device is in place on the formation sensor, the diffuser 14 is located in the beam 20 and the circular path of the index 7 cuts the diffused laser beam twice per rotation of the disk 8.

The cage 6, in addition to its protective function, likewise fulfills the function of retaining the means for attenuating and for diffusing the laser beam. In this embodiment, an opal or translucent glass 14 is used. The latter is situated in a plane perpendicular to the path of the laser beam, and thus in a plane parallel to the path which is normally followed by the sheet of paper. The diffuser 14, in addition to attenuating the laser beam, performs a spatial broadening function.

Turning now to the operation of the calibration device, rotation of the disk 8, at a constant speed imparts to the index 7, a periodic movement causing a modulation of the laser beam, said modulation being detected by the receiving system of the formation sensor situated at the end of the branch 2 of the chassis. On account of the design of the device according to the invention, the index 7 traverses the laser beam at two locations in the course of each rotation, and this takes place in two diametrically opposite positions, namely on the one hand adjacent the location of the diffuser, and on the other hand adjacent the location of the receiving system. The modulated radiation will have a different value, depending upon the place of traverse of the laser beam by the index 7.

Figure 4:
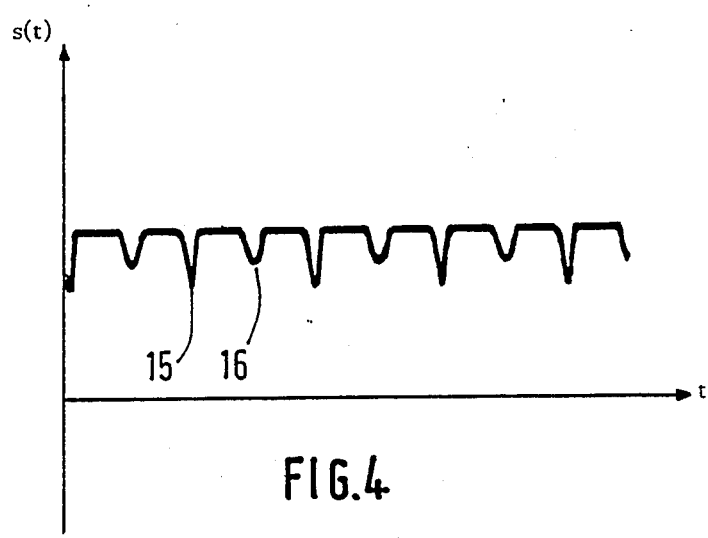
FIG. 4 is a graphical representation of the modulation curve obtained by means of the device according to the invention.

In FIG. 4, this modulated beam, as detected by the formation sensor in arm 2, is plotted as s(t) on the vertical axis against time on the horizontal axis and gives a known and arbitrary value from which the formation sensor in branch 2 may be calibrated. Thus, as can be seen in FIG. 4, the peaks 15 correspond to the traverse of the laser beam by the index 7 at the location of the diffuser 14, while the peaks 16 correspond to the traverse of the laser beam by the index 7 at the location of the detecting element of the formation sensor.

It should be noted that the form and the amplitude of these modulations may be determined as a function of the geometrical characteristics of the device and of the index 7. They are determined in such a manner that the spectrum of the modulation signal of the standard index 7 is situated towards the center of the RMS computation frequency band of the formation meter. Likewise, the speed of rotation of the disk is matched in such a manner that the modulation frequency generated by the passage of the index 7 is situated towards the center of said frequency band. Thus, slight variations of the speed of rotation of the disk 8 have no effect on the formation index computed by means of the standard index 7.

When the rotation of the disk is stopped, the diffuser 14 diffuses the beam 20 by a known amount corresponding to the unmodulated line in FIG. 4. Calibration of the formation sensor under this condition corresponds to a formation index of zero and permits setting of the optical zero level for the formation sensor in arm 2.

When the electronic processing, which is associated with the formation sensor of our prior referenced patent, is applied to the modulated signal produced by the calibration device, a constant value formation index is obtained.

Thus, the device according to the present invention is particularly suitable for calibrating devices for measuring the characteristics of a continuous web of paper given that only its mounting system varies in order to permit its placement on devices other than that described in the invention.

What is claimed is:

1. A device for calibrating a measuring apparatus in which an emitted light beam is directed through a sheet of paper which crosses the path of said light beam and in which the transmitted light beam is detected and processed into a modulated output signal comprising:
   means for constantly diffusing the emitted light beam to a broad, unfocused beam, light absorbing means rotatably mounted adjacent said emitted light beam for movement into and out of said beam, wherein said light absorbing means alternately intersects said beam at first and second positions along the axis of said beam;

said absorbing means being disposed to absorb a greater amount of emitted light in said first position within said beam and a lesser amount of emitted light in said second position within said beam;

so that rotation of said light absorbing means produces in said measuring apparatus a characteristic calibration modulation so that said measuring apparatus can be calibrated relative to said value.

2. A device according to claim 1 wherein said absorbing means comprises:

a rotatable disc mounted in a plane parallel to the axis of the emitted light beam; and a light absorbing rod mounted on said disc perpendicular thereto;

so that upon rotation of said disc, said rod intersects said emitted light beam a first time adjacent said diffusing means and a second time adjacent said sensor means for each revolution of said disc.

3. A device for calibrating a measuring apparatus as defined in claim 2 further including a balancing weight mounted on said disc on the opposite end of the diameter on which said rod is mounted to balance said disc and rod assembly upon rotation.

4. A calibrated device for measuring apparatus as described in claim 2 further defined by light shield means mounted adjacent said rotatable disc disposed to enclose said emitted light beam and light absorbing member as it is rotated through said emitted light beam so that spurious light sources are eliminated from any calibration of the measuring apparatus.

5. A device as described in claim 4 wherein said shield means comprises a truncated cylinder having a matte black finish on the interior thereof.

6. A device as described in claim 5 wherein said calibrating device includes clamping jaws for mounting the calibrating device on the measuring apparatus to be calibrated.

7. A device for calibrating a measuring apparatus in which an emitted light beam is directed through a sheet of paper which crosses the path of said light beam and in which the transmitted light beam is received and analyzed, comprising:

means for constantly diffusing the emitted light beam to a broad unfocused beam;

light absorbing means rotatably mounted adjacent said emitted light beam for movement into and out of said beam, wherein said light absorbing means alternatively intersects said beam at first and second positions along the axis of said beam;

said absorbing means being disposed to absorb a greater amount of emitted light in said first position within said beam and a lesser amount of emitted light in said second position within said beam;

means for periodically moving said absorbing means through said emitted light beam, and sensor means for detecting the transmitted light while said absorbing means is moved through said emitted light beam.

* * * * *